United States Patent [19]

Jalowayski

[11] Patent Number: 4,576,168

[45] Date of Patent: Mar. 18, 1986

[54] NASAL DILATOR

[76] Inventor: Alfredo A. Jalowayski, 6864 Lipmann St., San Diego, Calif. 92122

[21] Appl. No.: 455,651

[22] Filed: Jan. 5, 1983

[51] Int. Cl.[4] .............................................. A61M 29/00

[52] U.S. Cl. ...................................... 128/342; 128/11; 128/18

[58] Field of Search ............................... 128/3, 10-11, 128/17-19, 341-343, 345, 346, 321; 81/DIG. 6, 427; 16/225, 234, 302

[56] References Cited

U.S. PATENT DOCUMENTS

| | | | |
|---|---|---|---|
| 673,598 | 5/1901 | Dolge | 128/345 |
| 3,616,497 | 11/1971 | Esposito, Jr. | 128/346 |
| 3,636,954 | 1/1972 | Weston | 128/321 |
| 3,664,330 | 5/1972 | Deutsch | 128/342 |
| 3,906,957 | 9/1975 | Weston | 128/321 |
| 4,365,625 | 12/1982 | Rind | 128/345 |

FOREIGN PATENT DOCUMENTS

| | | | |
|---|---|---|---|
| 641398 | 6/1962 | Italy | 128/321 |
| 48112 | 12/1981 | U.S.S.R. | 604/158 |

OTHER PUBLICATIONS

The Surgical Armamentarium, American V. Mueller, p. 683, 1980.

*Primary Examiner*—C. Fred Rosenbaum
*Assistant Examiner*—Gene B. Kartchner
*Attorney, Agent, or Firm*—Albert L. Gabriel

[57] ABSTRACT

A nasal dilator compatible with conventional illuminating devices whereby the nasal passage may be symmetrically dilated allowing for even illumination for inspection of the nasal cavity or the insertion of a specimen collection probe. Two symmetrical lever arms are spring-urged together and connected to a common base by a pair of wing-like arc springs. Compression of these springs by an inward force on the proximal ends of the lever arms urges their distal ends apart expanding the nasal passage by means of two symmetrically projecting dilating members.

11 Claims, 9 Drawing Figures

35 38 14 39 36 10 32 26 32 24 26 34 34 46 22 30 16 20 30 12 28 28 42 44

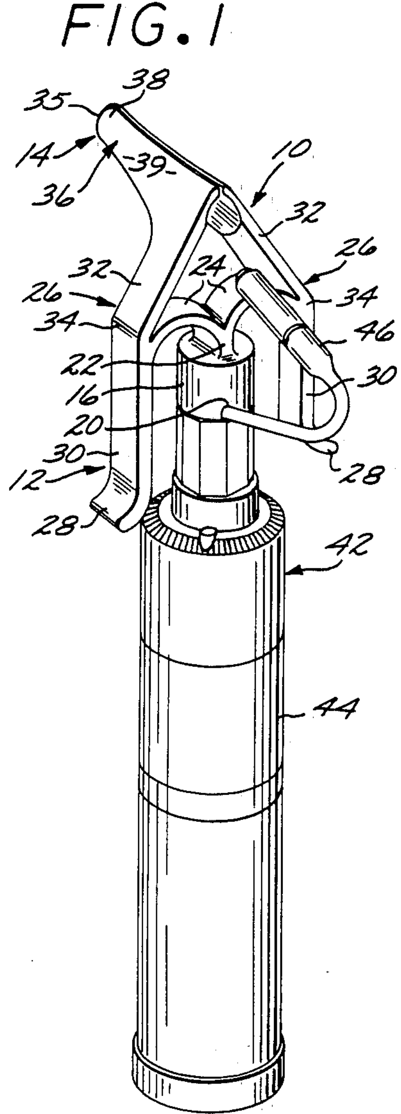
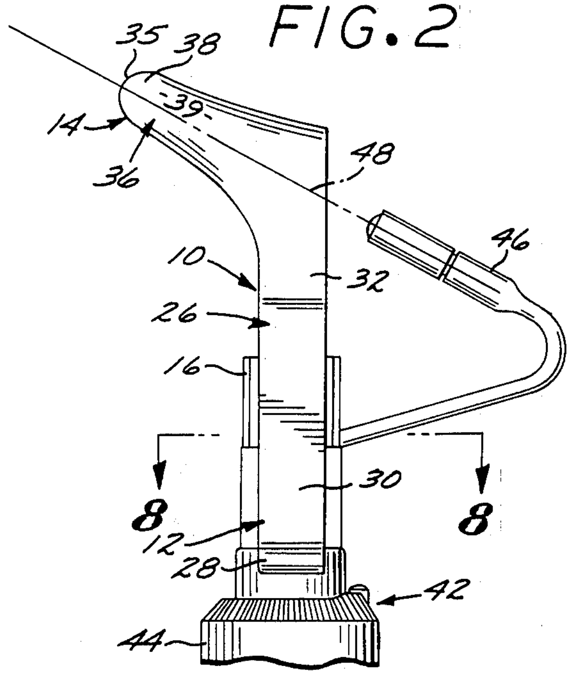
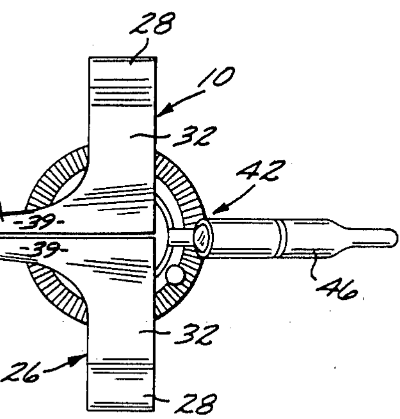
FIG. 3
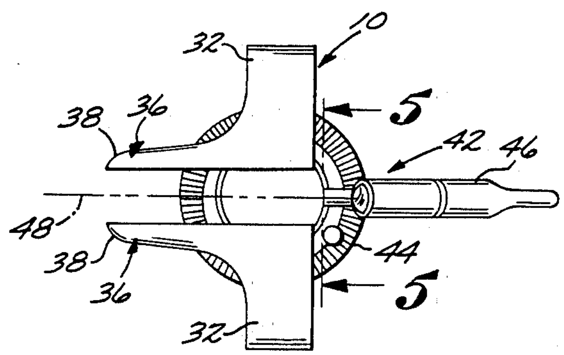
FIG. 4
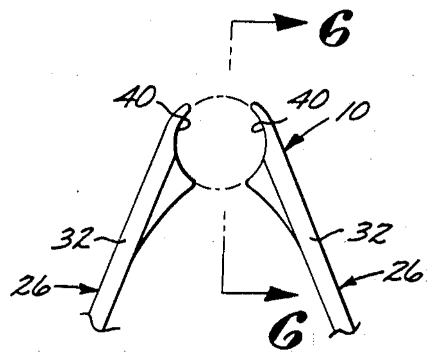
FIG. 5

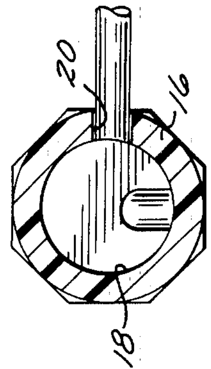
FIG. 8
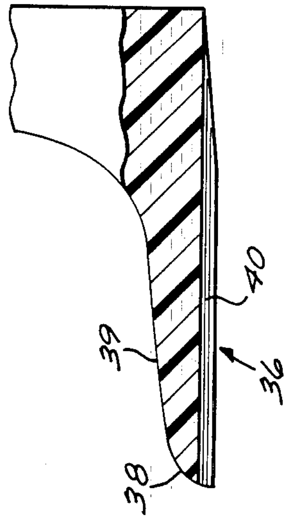
FIG. 7
FIG. 6
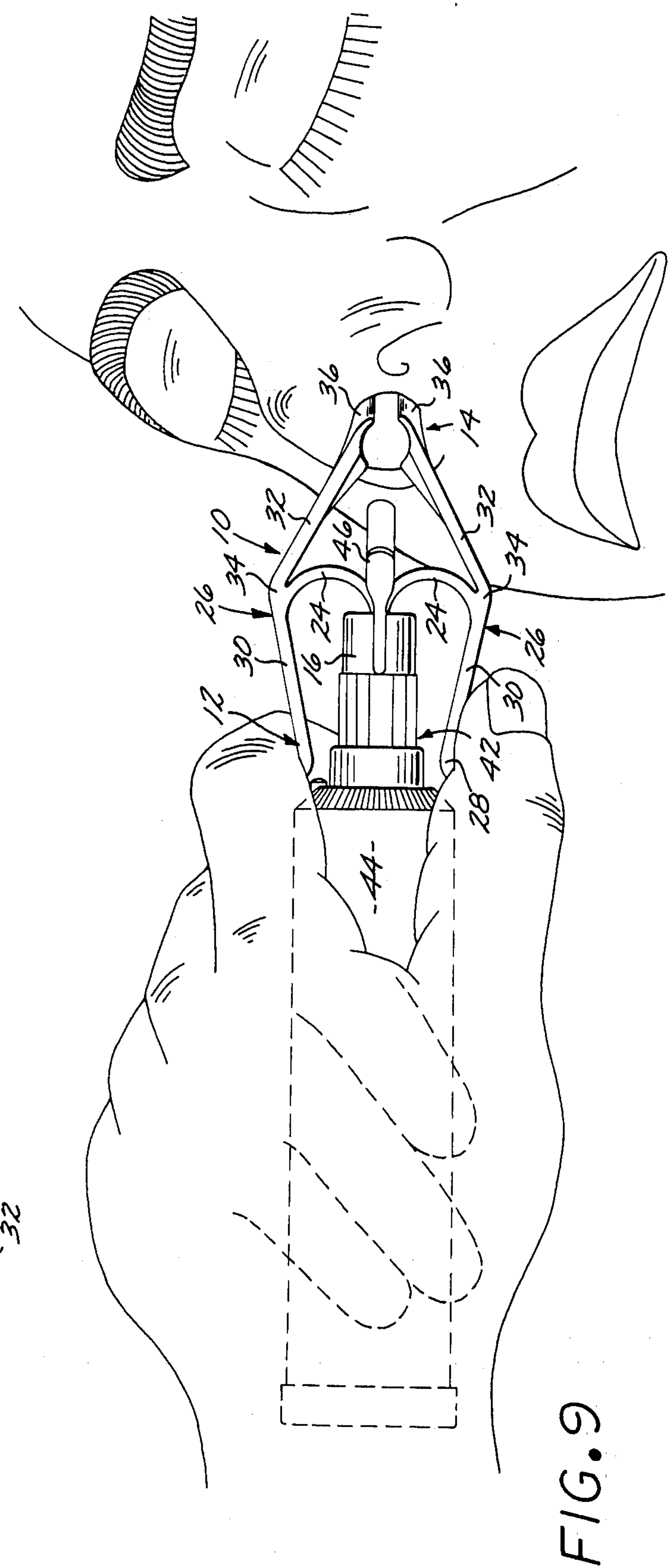
FIG. 9

NASAL DILATOR

BACKGROUND OF THE INVENTION

1. Field of the Invention

This invention is in the field of medical instruments, and relates in particular to nasal dilating instruments.

2. Description of the Prior Art

For the dilation of the nostril and lower nasal passage to facilitate examination thereof, the conventional prior art procedure is to employ a nasal speculum which attaches to an associated illuminating device. The conventional nasal speculum of the prior art is metal, having one fixed and one moveable jaw or spreader. The spreader jaw is unitarily joined at generally right angles with a lever grip. The spreader and lever pivot about a pin or other axis passed through their junction. The illuminating device and speculum attachment are grasped by the fingers while the thumb operates the lever grip and spreader. The speculum jaws are inserted into the patient's nostril and the spreader opened outward dilating the nostril. The illuminating device provides a beam of light which is directed into or toward the nasal passage in order to facilitate examination. The speculum/illumination assembly is biased for use by one hand or the other due to the asymmetrical configuration of fixed jaw, spreader and lever grip.

The use of metal in producing a speculum for use in dilating the nasal passage has several drawbacks. It is costly and therefore makes an adequate supply of specula financially untenable in any but a large clinic. The metal specula must be marketed as reusable items making it necessary to sterilize them between usages. In a busy clinic this is impractical and sterilization is therefore frequently inadequately effected by the use of an autoclave. The insertion of metal speculum jaws is often uncomfortable due to the coldness of the metal. Finally, the light reflective qualities of metal jaws confuse the passage of the light beam into the nostril and hinder the physician in his examination.

The asymmetry of the conventional speculum also provides difficulties. Besides biasing the use of the speculum/illuminator assembly toward use in one hand or the other, the opposition of a moveable jaw with a fixed jaw causes the nostril to be unevenly dilated when the speculum jaws are opened. Centering a light beam along a nasal passage thus dilated is extremely difficult. The physician has little chance of gaining a clear, unobstructed view of the nasal interior. Also, the fixed jaw partially obstructs the light beam and therefore reduces the amount of light which reaches the nasal objective.

Attempts to improve the prior art procedure for dilating the nasal passages are disclosed in U.S. Pat. Nos. 1,014,076; 1,595,378; 1,695,107; 3,664,330; 3,841,318; and 4,201,217. Disclosed in U.S. Pat. Nos. 1,041,076 and 4,201,217 are devices intended to facilitate breathing, especially while asleep and prevent the collapse or other closure of the nasal passages. These devices are not suitable for the examination of the nasal interior insofar as their very insertion visually obstructs the nostril opening. U.S. Pat. No. 1,695,107 shows an invention intended for the heat treatment of the interior nasal tissues. The lamps are extended on arms that open due to a ratcheting device. The lamps provide no usable illumination themselves and the general configuration of the device makes it unsuitable for use as a speculum. A fiber optic tool is disclosed in U.S. Pat. No. 3,774,330 and is comprised in part by a speculum of fiber optic material, light cable, and microscope-like viewing lenses. The device overcomes none of the difficulties of cost, sterilization, or one-time use while introducing a number of cumbersome and limiting mechanical details. A vaginal speculum of unitary construction having dual speculum legs is disclosed in U.S. Pat. No. 3,841,318. The legs of this device are spread apart in its position of repose—i.e., it is biased to its open position—so that this device could not be used for dilation of the nasal passage nor adapted to one-handed use in conjunction with an illuminating device. In U.S. Pat. No. 1,595,378 a speculum/illuminator assembly with dual spreader jaws forced open by a ratchet and thumb-activated similarly to the conventional art is disclosed. The jaws provide no aperture for the insertion of any probe intended for collection of specimens from or manipulation of the nasal passage.

None of these prior art devices provide a suitable non-light reflective, disposable speculum for the symmetrical dilation of the nasal passage allowing for proper illumination of the passage and insertion of a specimen collection probe.

SUMMARY OF THE INVENTION

In view of these and other problems in the art, it is the general object of the present invention to provide a disposable nasal dilator suitable for use in conjunction with conventional nasal illuminating devices.

Another object of the present invention is to provide a disposable nasal dilator that dilates the nasal passage symmetrically by use of dual opposing lever arms.

Another object of the invention is to provide a nasal dilator of the above character which makes efficient use of conventional illuminating devices by centering the beam of light thereby provided along the interior of the nasal passage.

Yet another object is to provide a nasal dilator of the above character which cooperates with the natural contours of the nose by having dilating members which conform to the interior of the nostril and angle along the nasal passage so as to provide clear passage of a light beam.

A further object is to provide a nasal dilator of the above character which may be used with equal facility in either hand.

A still further object is to provide a nasal dilator of the above character with dilating members scaled down in such a way as to make its use convenient for pediatric examinations while still fitting the conventional illuminating device.

The nasal dilator of the present invention is of unitary molded construction. The base of the nasal dilator is suitable for mounting upon a conventional nasal illumination device. Two bilaterally symmetrical lever arms are connected to the base and spring-biased together at their distal ends by a bilaterally symmetrical pair of wing-like arc springs. The distal ends of the lever arms may be urged apart by pressing their proximal ends together. At the distal ends of the lever arms project symmetrical dilating members. These distal dilating members are angled in such a way as to allow easy insertion into the nasal passage. Therefore, by pressing together the proximal ends of the lever arms, the nasal passage is symmetrically dilated along its natural angle. The aperture formed by the dilation of the dilating members and nasal walls allows the unobstructed passage of a light beam provided by a compatibly angled conventional illuminating device. The aperture thus formed also allows for the insertion of a mucous or mucosal specimen collection probe into the nasal passage for collection at the appropriate site.

BRIEF DESCRIPTION OF THE DRAWINGS

These and other objects of the invention will become more apparent in reference to the following description and the accompanying drawings, wherein:

FIG. 1 is a perspective view showing the nasal dilator of the invention operatively connected to a conventional nasal illuminator;

FIG. 2 is a side elevational view of the nasal dilator connected to the nasal illuminator, with the latter shown in fragmentary elevation;

FIG. 3 is a top plan view of the nasal dilator and nasal illuminator combination showing the dilating members in a closed position;

FIG. 4 is an view similar to FIG. 3 showing the nasal dilator with its dilating members in a spread-apart dilating position;

FIG. 5 is an fragmentary sectional view taken on the line 5—5 in FIG. 4;

FIG. 6 is an enlarged, fragmentary sectional view taken on the line 6—6 in FIG. 5;

FIG. 7 is a fragmentary sectional view, partly in elevation, taken on the line 7—7 in FIG. 6;

FIG. 8 is an enlarged, fragmentary horizontal section taken on the line 8—8 in FIG. 2; and FIG. 9 is an elevational view showing the nasal dilator of the invention and an associated nasal illuminator in operation for the dilation and illumination of a nasal passage.

DETAILED DESCRIPTION

Referring to the drawings, and at first particularly to FIGS. 1 to 4 thereof, the nasal dilator of the present invention is generally designated 10, and is of unitary construction having a proximal end 12 and a distal end 14. Two wing-like arc springs 24 are attached to a common base 16. The arc springs 24 are band-like and may be compared mechanically to very short sections of a watch spring. They are joined symmetrically to the top of the base 16 forming a shared and fixed fulcrum axis 22 along that junction. The arc springs 24 are of equal natural curvature with their convex sides facing generally in the distal direction, and are bilaterally symmetrical in every way. Each joins, at its outer extremity, with a lever arm 26. These lever arms 26 are bilaterally symmetrical, opposing and are urged together at their distal, or in this case upper, ends by the arc springs 24. (See FIG. 1 for the above.)

Here, as elsewhere in this description, vertical dimensions (top, bottom, upper, lower, etc.) are arbitrarily assigned and made uniform in order to facilitate and clarify the disclosure of the present invention and it is to be understood that these terms have not been used by way of limitation. Dimensions of proximity (proximal, distal) are assigned according to the frame of reference of a physician or technician and the hand or other instrument with which he manipulates the present invention during its use. Centrical dimensions (inner, inward, outer, outward) refer to the plane of symmetry of the present invention as central.

The proximal or lower ends of the lever arms 24 extend below the base 16 and terminate in outwardly flared finger grips 28 (see FIG. 1). These finger grips 28 are contiguous with what are substantially parallel segments 30 of the lever arms 26. The parallel arm segments 30 of the opposing lever arms 26 give way in each arm at a bend joint 34 to symmetrically converging arm segments 32 which culminate in an apical contact point 35 where the opposing lever arms 26 touch at their upper or distal extremities.

The arc springs 24 are compressed into an increased curvature or tightness by forcing the two finger grips 28 toward each other. The upper or distal ends of the lever arms 26 are thereby spread apart. The lever arms 26 are joined immediately below their bend points 34 to the arc springs 24 in a fixed, generally tangential orientation. This configuration provides a large mechanical advantage in bending the arc springs 24 and hence in spreading the lever arms 26 outward from their apical contact point 35, as indicated by the fact that there is only a very small increment of bending movement in each of the springs 24 that results from a relatively large inward swinging movement of the lever arm finger grips 28.

Extending from the upper ends of the lever arms 26 distally along the plane of symmetry of the nasal dilator 10 herein described, at preferably approximately 30° above the horizontal as defined by the fulcrum axis 22 of the arc springs 24, are two elongated, symmetrical and generally parallel dilating members 36. Thus, the dilating members 36 are angularly offset at a preferred angle of inclination of approximately 60° relative to the general longitudinal axes of the lever arms 26. The dilating members 36 have tapering, convexly rounded outwardly facing surfaces 39 with rounded distal ends 38 (FIGS. 2, 3, 6, 7). When not spread apart by inward force exerted upon the finger grips 28, the dilating members 36 make contact along their upper edge—also the apical contact point 35. Thus, the springs 24 support the lever arms 26 in a normal position of repose in which the dilating members 36 are in a substantially closed-together position. When mated in this manner, it is possible to easily and safely insert the dilating members 36 into a nostril, even with the relatively delicate tissues that are present. The increasing expansion of the dilating members 36 toward their base follows the approximate contours of the nostril interior. Once the dilating members 36 have been inserted, the nostril can be dilated by forcing the finger grips 28 at the proximal ends of the lever arms 26 together. This is the essential action of the present nasal dilator 10 and the general purpose of any adequate speculum to be used in the examination of the nasal passages.

The base 16 of the nasal dilator 10 has a recessed socket 18 in its underside. This socket 18 allows the nasal dilator 10 to be mounted on a conventional illuminating device 42 of the sort commonly used in the examination of the nasal passages and available from Welch-Allyn Corp. of Skaneateles Falls, N.Y. (see FIGS. 1, 2 and 9). This conventional illuminating device has a generally cylindrical battery pack 44 which serves as a handle, with a bulb extension 46 extending in a gooseneck configuration from its upper end. The nasal dilator 10 is properly oriented on the top of battery pack 44 by means of a downwardly opening notch 20 in the recessed socket 18 allowing passage for the bulb extension 46 whereby the light is shone along an angle suitable for illumination of the nasal passages (see FIGS. 1 and 2). In FIGS. 1 to 4 and 9, the present nasal dilator 10 is shown in conjunction with such a conventional illuminating device 42. FIGS. 1, 2 and 9 disclose the compatability of the angled dilating members 36 with the upwardly inclined direction of illumination of the bulb extension 46 indicated by the phantom line 48 in FIGS. 2 and 5.

The inward facing surfaces 40 of the dilating members 36 are chordally grooved as shown in FIGS. 1, 5, 6 and 9. When the upper ends of the lever arms 26 are spread, the matching concavities of the inner surfaces 40 of the dilating members 36 open an aperture suitable for the unobstructed passage of a light beam provided by the illuminating device 42 along the direction of the phantom line 48. (See FIGS. 4 and 5). This aperture also allows for the insertion of a mucosal specimen collection probe.

The symmetrical spread of the dual lever arms 26 and consequently of the dilating members 36 insures the even, unobstructed illumination of the nasal passage. The symmetrical separation of the lever arms 26 also allows the light beam indicated by phantom line 48 to be centered along the passage defined between inward facing surfaces 40. When mounted on a conventional illuminating device 42, experience shows that it is natural and comfortable to grip and steady the speculum attachment between the thumb and forefinger, while the second, third and fourth fingers grasp the bulk of the battery pack 44. The present nasal dilator 10 exploits this natural impulse of the physician or technician by matching opposing dual lever arms 26 to the opposition of thumb and forefinger. The present nasal dilator 10 becomes a natural extension of the technician's hand. The symmetry of the nasal dilator 10 also allows the device to be used with equal facility in the left or right hand.

In the preferred embodiment of the present invention, the nasal dilator 10 is molded of an inexpensive, resilient plastic material having good elastic memory characteristics, such as nylon or the like. This allows the nasal dilator 10 to be distributed for one-time use. The disposability of the present invention circumvents the inconvenience of sterilization for reuse and the danger of infection presented by improper or inadequate sterilization. Also, the use of a non-metallic material in producing the present nasal dilator 10 eliminates any reflection of light that may occur with a metal speculum and hinder a clear view of the nasal passage. It also eliminates the discomfort frequently caused by contact of cold metal parts against warm, sensitive nasal tissues.

Another embodiment of the present invention is that in which the dilating members 36 are made smaller for use in pediatric examination. Since the dilating members 36 of the present nasal dilator 10 are spring-urged together, the examining physician can easily control the amount of pressure exerted on a child's nasal passage and avoid injury to the young patient. The rounded sides of the dilating members 36 greatly reduce the chances of damaging the delicate tissues of a child's nose.

It is important that the nasal dilator 10 as disclosed herein be molded of a sufficiently resilient material to provide a strong and stable spring for the wing-like arc springs. The symmetrical tension in these springs insures the symmetrical spread of the lever arms 26 and hence the dilating members 36. It is this symmetrical spread of the dual lever arms 26 and dilating members 36 that allows the unobstructed beam of light to be centered along the nasal passage.

While the present invention has been described with reference to presently preferred embodiments, it is to be understood that various modifications or alterations may be made by those skilled in the art without departing from the scope and spirit of the invention as set forth in the appended claims.

I claim:

1. A disposable nasal dilator which comprises:

a pair of elongated, spaced-apart, generally bilaterally symmetrical lever arms having proximal and distal ends;

a pair of opposed, generally parallel, elongated dilating members projecting from said distal ends of the respective said lever arms; and spring means extending laterally between said lever arms, said spring means and said pair of dilating members being of unitary molded plastic construction with said spring means being substantially rigidly secured to both of said lever arms at substantially the same locations along their lengths intermediate their ends;

said spring means constituting the sole supporting means for said lever arms;

said spring means supporting said lever arms in a normal position of repose in which said dilating members are in a substantially closed-together position;

movement of said proximal ends of said lever arms toward each other against the force of said spring means causing said dilating members to spread apart to an open position for dilating a nasal passage.

2. A nasal dilator as defined in claim 1, wherein said spring means is substantially bilaterally symmetrical.

3. A nasal dilator as defined in claim 2, wherein said spring means comprises a pair of wing-like arc springs rigidly joined together at a central location between said lever arms.

4. A nasal dilator as defined in claim 3, wherein said arc springs are bowed with their convex sides facing generally in the distal direction.

5. A nasal dilator as defined in claim 2, wherein said spring means is connected to said lever arms at approximately their longitudinal centers.

6. A nasal dilator as defined in claim 2, wherein each of said lever arms terminates at its proximal end in an outwardly flared finger grip.

7. A nasal dilator as defined in claim 2, wherein the general longitudinal axes of said dilating members are angularly offset at a substantial angle of inclination relative to the general longitudinal axes of said lever arms.

8. A nasal dilator as defined in claim 7, wherein said dilating members are generally arcuate in transverse section, having outwardly facing convex surfaces, and having opposed, inwardly facing concave surfaces which define a viewing passage therebetween when said dilating members are in their said open position.

9. A nasal dilator as defined in claim 8 which comprises a base to which said spring means is substantially rigidly connected proximate the bilateral center of said spring means;

said base defining a socket that opens generally in the proximal direction and is adapted for coupling said nasal dilator to a nasal illuminating device having a bulb extension that is capable of directing a beam of light generally coaxially through said viewing passage.

10. A nasal dilator as defined in claim 9, wherein said spring means comprises a pair of wing-like arc springs connected to and extending laterally outwardly from said base.

11. A nasal dilator as defined in claim 10, wherein said arc springs extend generally distally from said base and are bowed with their convex sides facing generally in the distal direction.

* * * * *